(12) United States Patent
Trachsel

(10) Patent No.: US 10,744,026 B2
(45) Date of Patent: Aug. 18, 2020

(54) URINE DIRECTIONAL SYSTEM

(71) Applicant: Kirk Trachsel, Las Vegas, NV (US)

(72) Inventor: Kirk Trachsel, Las Vegas, NV (US)

(*) Notice: Subject to any disclaimer, the term of this patent is extended or adjusted under 35 U.S.C. 154(b) by 0 days.

(21) Appl. No.: 16/415,280

(22) Filed: May 17, 2019

(65) Prior Publication Data

US 2019/0350746 A1 Nov. 21, 2019

Related U.S. Application Data

(60) Provisional application No. 62/673,685, filed on May 18, 2018.

(51) Int. Cl.
*A61F 5/451* (2006.01)

(52) U.S. Cl.
CPC .................... *A61F 5/451* (2013.01)

(58) Field of Classification Search
CPC ........................................ A61F 5/451
USPC ............................... 4/144.1–144.4
See application file for complete search history.

(56) References Cited

U.S. PATENT DOCUMENTS

| 4,531,245 A | * | 7/1985 | Lowd | A47K 11/00 141/337 |
| 4,822,347 A | * | 4/1989 | MacDougall | A61F 5/455 604/329 |
| 4,985,940 A | * | 1/1991 | Jones | E03D 13/002 4/144.1 |

* cited by examiner

*Primary Examiner* — Lauren A Crane
(74) *Attorney, Agent, or Firm* — Cislo & Thomas, LLP

(57) ABSTRACT

A urine directional system to guide the direction of urine flow, the system having a urine directional device having a generally elongated tubular object that is flexible, extendable, and compressible, and a cap that makes contact with the user, the cap being comfortable to the touch. The urine directional device can also have segments of rigid tubing that is integrally formed with or attached at opposite ends of the tubular object to provide sturdiness to the device. The device can also have a screen at one end of the device to catch solid objects in the urine. The system can also have a holder to hold and store the urine directional device. The holder can have a removable container located at the bottom of the holder to catch drips from the device.

18 Claims, 6 Drawing Sheets

URINE DIRECTIONAL SYSTEM

CROSS-REFERENCE TO RELATED APPLICATION

This patent application claims the benefit of U.S. Provisional Patent Application Ser. No. 62/673,685, entitled "Male Penile Urine Directional System," filed May 18, 2018, which application is incorporated in its entirety here by this reference.

TECHNICAL FIELD

The invention described herein generally relates to a mechanical device to assist typically older males in urinating directly into a urinal, toilet, or the like without making a mess on themselves or the immediate surroundings, and a receptacle to contain such a device.

BACKGROUND

Many older males have a problem when they urinate—namely, they have a difficult time extracting their penis from their pants and underwear. As a result, in such situations while urinating, urine would miss the toilet and wind up on a male's pants or elsewhere, such as the floor or rim of the toilet.

Today, more than ever, there is much caregiving, either through friends, family members, or hired caregivers for the elderly, including elderly males. It is not only a challenging and potentially unsanitary situation to have urine that winds up on a man's clothes or on the toilet or floor, but the situation is also difficult, inconvenient, and potentially emotionally uncomfortable and/or embarrassing for the male and the caregiver when "off-target" urination occurs and needs to be cleaned. The invention described herein is intended to address these challenges by providing a new device to assist aging males in urinating directly into a urinal, toilet, or the like without making a mess on themselves or the immediate surroundings.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1A:
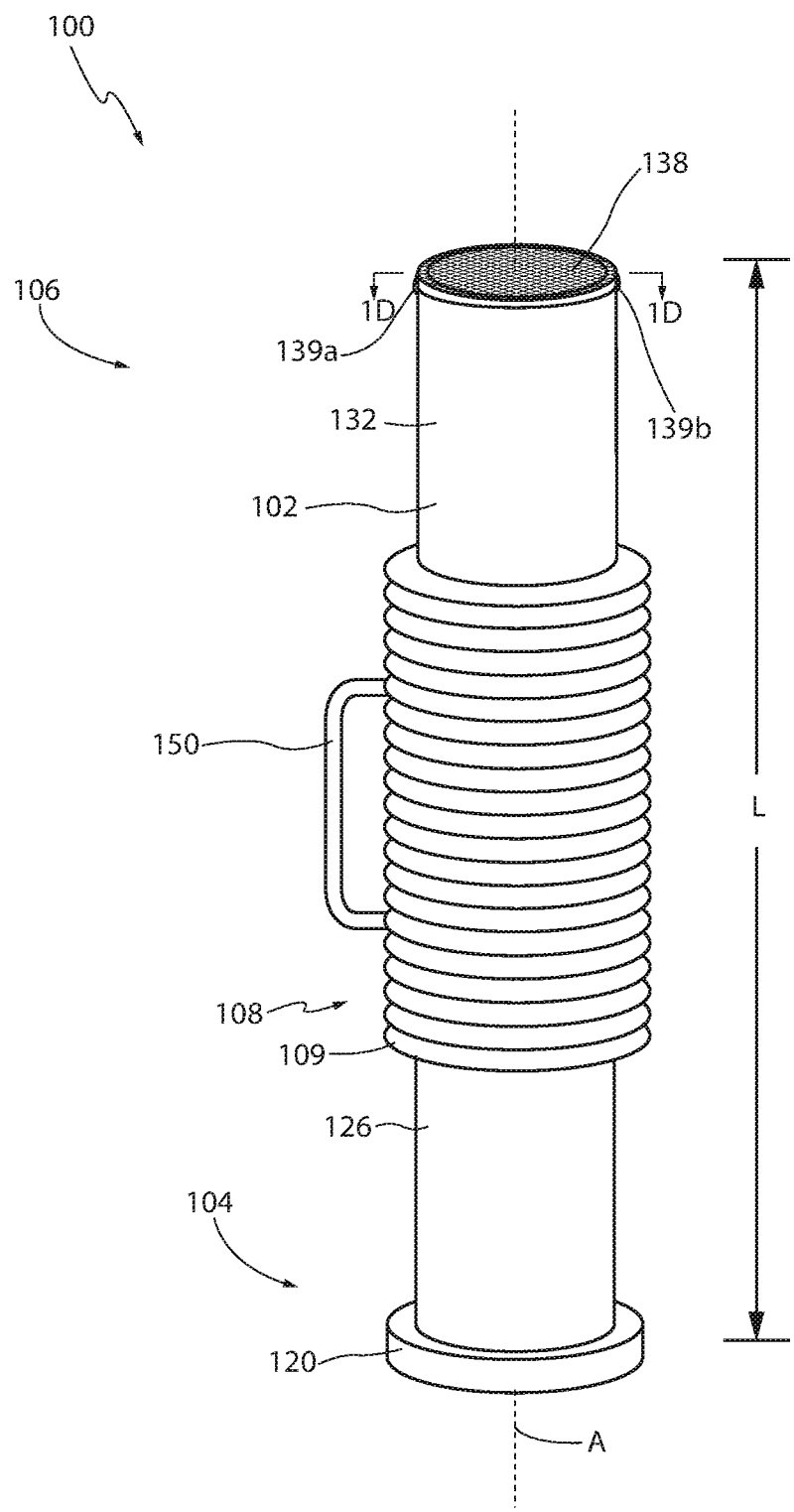
FIG. 1A is a perspective view of an embodiment of a urine directional device.
Figure 1B:
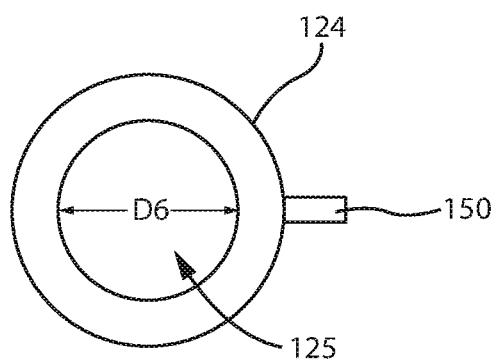
FIG. 1B is a bottom view of the urine directional device.
Figure 1C:
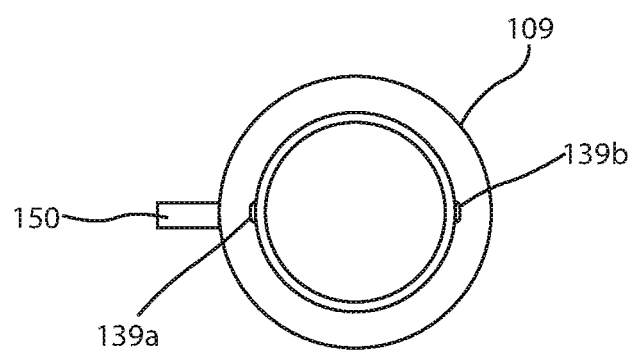
FIG. 1C is a top view of the urine direction device.
Figure 1D:
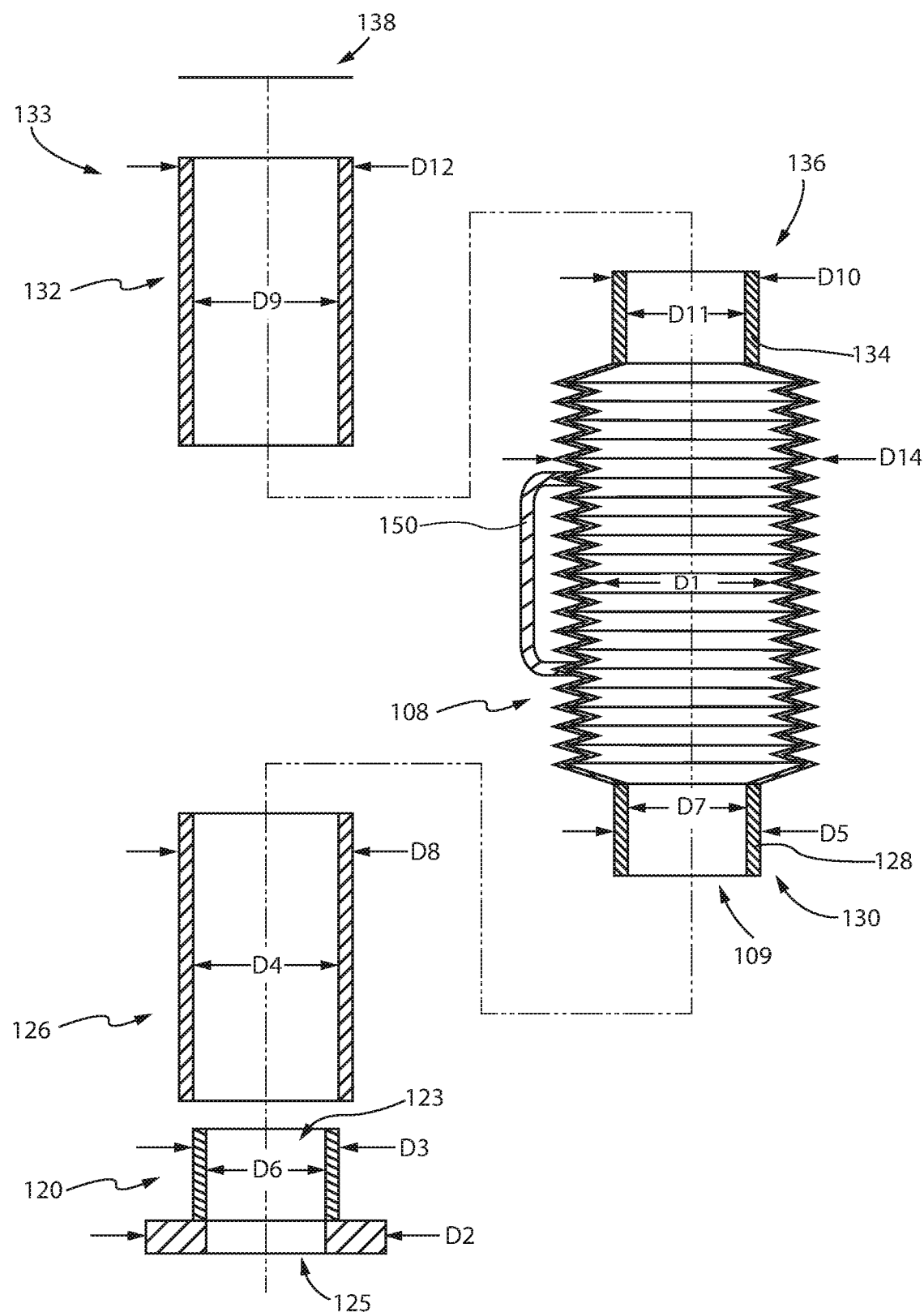
FIG. 1D is a cross-sectional, exploded view from the side take along line 1D-1D shown in FIG. 1A.
Figure 2:
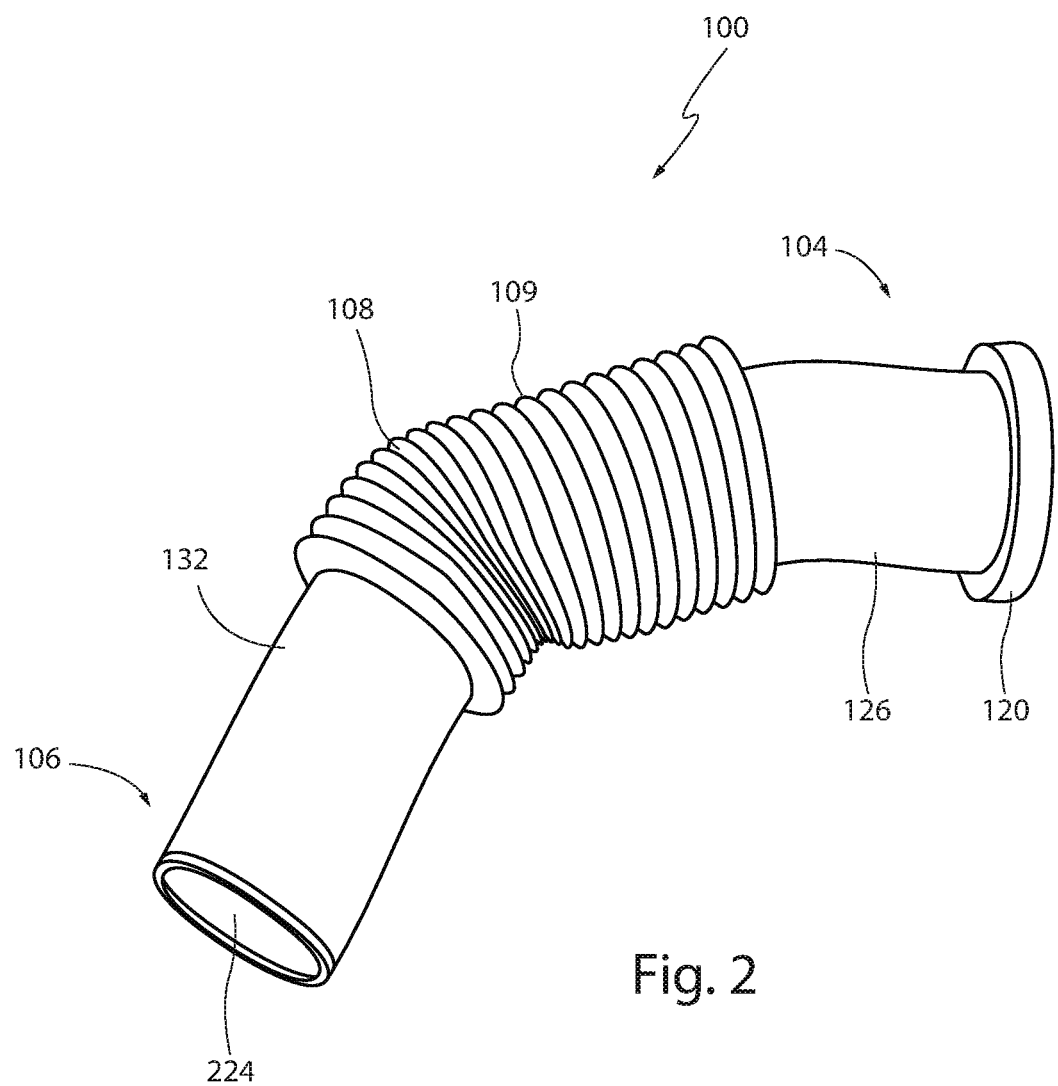
FIG. 2 is another embodiment of the urine directional device.

As shown in FIGS. 1A-2 appended hereto, but without intention of being so limited, the urine directional device 100 is generally a tube 102 having a proximal end 104 and a distal end 106 opposite the proximal end 104, the tube 102 defining a central axis A for the purpose of guiding or directing the flow of urine by a user. The tube 102 comprises a generally elongated tubular object 108 having a first end 130, a second end 136, and a body 135 therebetween. In the preferred embodiment, the body 135 can be flexible, whereas the first end region 130 and the second end region 136 can be rigid.

The generally elongated tubular object 108 is preferably formed of material that is impermeable to aqueous solutions, yet allows the body 135 to retain a level of flexibility so that the elongated tubular object 108 can be bent in a variety of different direction with minimal effort. Thus, if the urine directional device 100 shown in FIG. 1A was held at the proximal or distal ends 104, 106 such that the central axis A was parallel to the ground, there would be noticeable bending at the body 135 of the elongated tubular object 108 as shown in FIG. 2. By way of example only, the generally elongated tubular object 108 can be formed of rubber that is impermeable to diffusion of aqueous solutions through it. In another embodiment, the elongated tubular object 108 can be made from plastic material. The elongated tubular object 108 can be formed of any other flexible, aqueous-impermeable material that is FDA approved. In a preferred embodiment, the body 135 of the elongated tubular object 108 can comprise an accordion tube. As such, the accordion tube has ribbing 109 that not only allows the elongated tubular object 108 to bend in a variety of different directions, but also allows the elongated tubular object 108 to expand and contract, thereby effectively elongating and shortening the length L of the elongated tubular object 108.

The length L of the tubular object 108 is preferably longer than a man's penis, and long enough to reach or approximately reach a toilet bowl when a man is standing, sitting, or lying adjacent to a toilet to urinate. Due to the ability of the elongated tubular object 108 to extend and contract, the length L of the elongated tubular object 108 can grow approximately two times, three times, four times, five times or more, the length of the elongated tubular object 108 when it is in its fully contracted state.

The length L and the cross-sectional diameter D1 of the elongated tubular object 108 is sufficient to encompass a man's penis, but still be easily handled by human hands. By way of example only, the length L of the elongated tubular object 108 in its contracted state can range from approximately 5 inches to approximately 20 inches in length. Preferably, the length L of the tubular object 108 in its contracted state can range from approximately 8 inches to approximately 15 inches. In a preferred embodiment, the length L of the elongated tubular object 108 in its contracted state can be approximately 10 inches to approximately 12 inches. The diameter D1 of the elongated tubular object 108 may be approximately 2 inches to approximately 8 inches. Preferably, the diameter D1 of the elongated object 108 is approximately 2.5 inches to approximately 7 inches. More preferably, the diameter D1 of the elongated object 108 is approximately 3 inches to approximately 6 inches. The dimensions can be further modified according to the needs and circumstances of the desired use.

In some embodiments, the elongated tubular object 108 may have a first portion 128 at the first end 130, and a second portion 134 at the second end 136. The first portion 128 and the second portion 134 can be integrally formed with the body 135 of the elongated tubular object 108. Preferably, the first portion 128 and the second portion 134 are rigid, meaning the first portion 128 and the second portion 134 do not bend under their own weight. Thus, the first portion 128 and the second portion 134 can be made of thicker or denser material than the body 135. Alternatively, the sizing of the first and second portions 128, 134 can be such that it becomes rigid.

The first and second portions 128, 134 can each be approximately 1.5 inches to 4 inches. Preferably, the first portion 128 and the second portion 134 can each be approximately 2 inches to approximately 3.5 inches. In some embodiments, the first portion 128 and the second portion 134 can be approximately 2.5 inches each. The body 135 can be approximately 2 inches to approximately to approximately 17 inches. In some embodiments, the body 135 can be approximately 3 inches to approximately 9 inches. In some embodiments, the body 135 can be approximately 6 inches.

As shown in FIGS. 1A-2 appended hereto, but without intention of being so limited, the urine directional device 100 also comprises a cap portion 120 operatively connected to the elongated tubular object 108 at the proximal end 104. Operatively connected is to be construed broadly so as to encompass a connection that allows the two components to have a functional relationship. Operatively connected can mean that two components are a single, integrally formed piece, or separate components fastened together permanently or in a manner that allows the components to be separated or disassembled.

That cap portion 120 may be a gasket, seal, or other similar object. Because the cap portion 120 is intended to make physical contact with the user, the cap portion 120 is preferably made of material that is comfortable when placed on the user. For example, the material can be soft, flexible, pliable, deformable, elastic, and the like, thereby providing padding or cushioning to the user. As such, the cap portion 120 may comprise rubber, plastic, silicon, and the like, or any other FDA approved material.

Figure 3:
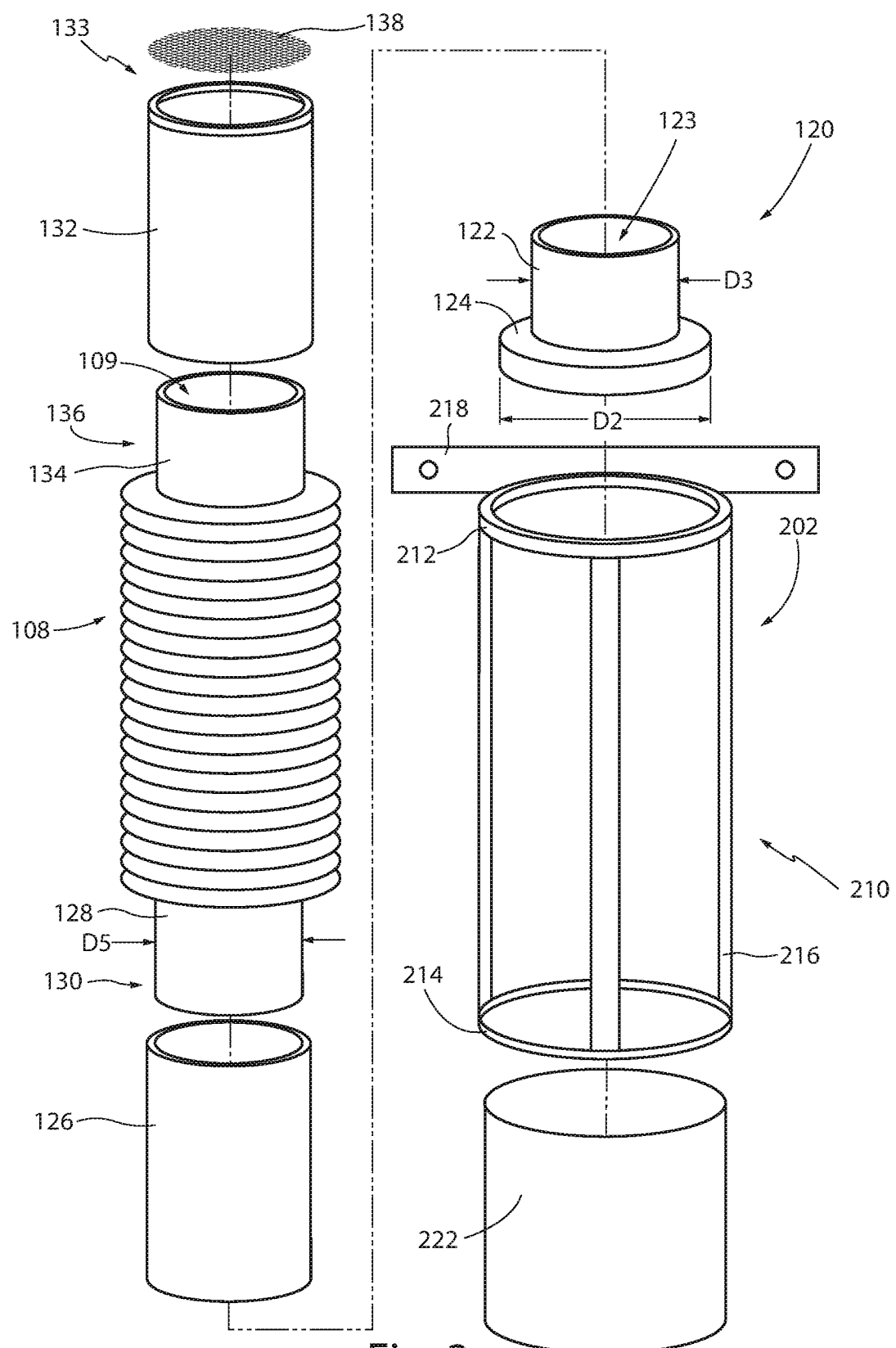
FIG. 3 is an exploded view of the urine directional system, including a holder.

In some embodiments, as shown in FIGS. 1D and 3, the cap portion 120 comprises a hollow post 122 and a flanged base 124 towards the proximal end 104, wherein the flanged base 124 has a diameter D2 greater than an exterior diameter D3 of the hollow post 122. In the preferred embodiment, the hollow post 122 is used to attach the cap portion 120 to the elongated tubular object 108. As such, the cap portion 120 may be a generally rigid structure to provide structural support when attaching to the elongated tubular object 108. The flanged base 124, however, can be made of material that is comfortable against the skin of the user. Thus, the flanged base 124 can comprise rubber, plastic, silicone, plastic, and the like, or any other FDA approved material. The flanged base 124 and the post 122 can also be made of the same material. The flanged base 124 defines an opening 125 that is continuous with an opening 123 of the hollow post 122, which in turn is continuous with the opening 109 of the elongated tubular object 108.

In some embodiments, the urine directional device 100 can comprises a first segment of tubing 126 surrounding the first portion 128 of the generally elongated tubular object 108 at a location generally adjacent to a first end 130 of the generally elongated tubular object 108. As such, the first segment of tubing 126 may also be in the form of a hollow tube. The first segment of tubing 126 may or may not be connected to the cap portion 120.

In some embodiments, the first segment of tubing 126 may have an interior diameter D4 that is substantially similar to the exterior diameter D3 of the hollow post 122 of the cap portion 120. Thus, the cap portion 120 may be secured to the first segment of tubing 126 by resistance fit. The resistance fit also creates a watertight seal to prevent any liquid from leaking out from in between the first segment of tubing 126 and the cap portion 120. Similarly, the interior diameter D4 of the first segment of tubing 126 may be substantially similar to the exterior diameter D5 of the first portion 128 of the elongated tubular object 108. This sizing allows the first segment of tubing 126 to connect with the first portion 128 of the elongated tubular object 108 via resistance fit in a manner that prevents liquids from leaking out from in between the first segment of tubing 126 and the elongated tubular object 128.

The operative connection of the first segment of tubing 126 to the cap portion 120 and the elongated tubular object 108 can be reversed in that the interior diameter D6 of the hollow post 122 and/or the interior diameter D7 of the first portion 128 of the elongated tubular object 108 can be substantially similar to the outer diameter D8 of the first segment of tubing 126 for a resistance fit. In the event a resistance fit seal or a watertight seal is not created at the operative connections between the cap 120 and the first segment of tubing 126 or the elongated tubular object 108, or between the first segment of tubing 126 and the elongated tubular object 108, a sealant can be used to create a watertight seal or to secure the aforementioned components together.

The first segment of tubing 126 is preferably substantially rigid tubing being comprised of a plastic, PVC, metal, or similar materials to provide at least a modicum of structural rigidity to the device 100 to facilitate use and storage of the device 100. In other words, if the device 100 was solely or primarily comprised of unreinforced, flexible material, it would likely be more difficult to use for its intended purpose. The extent of rigidity would be such that the first segment of tubing 126 would resist being bent during normal use in a manner that causes the first segment of tubing 126 to change direction under its own weight when suspended. By contrast, the elongated tubular object 108 is flexible to the extent that during normal use, the elongated tubular object 108 can be bent by a user to easily change its direction along the X-Y-Z coordinates. Thus, in some embodiments, the first portion 128 may also be flexible or not very rigid, to connect with the cap 120, and the first segment of tubing 126 may provide structural reinforcement at the connection between the elongated tubular object 108 and the cap 120.

As such, the first segment of tubing 126 may be operatively connected to the cap portion 120 as well as to the generally elongated tubular object 108. Thus, the first segment of tubing 126 may be a connecting bridge between the elongated tubular object 128 and the cap portion 120, or it can be a form of a reinforcing sleeve around the first portion 128 of the elongated tubular object 108, with the first portion 128 operatively connected to the cap portion 120. In some embodiments, the first segment of tubing 126 would not surround the tubular object 108, but solely be connected to it to form the continuous tubular structure of the overall device 100.

As shown in FIGS. 1A-2 appended hereto, but without intention of being so limited, the urine directional device 100 may further comprise a second segment of tubing 132 surrounding the second portion 134 of the generally elongated tubular object 108 at a location generally at a second end 136 of the generally elongated tubular object 108. The second segment of tubing 132 may or may not be connected to the second portion 134 of the elongated tubular object 108.

In some embodiments in which the second segment of tubing 132 is separable from the elongated tubular object 108, the second segment of tubing 132 may have an interior diameter D9 that is substantially similar to the exterior diameter D10 of the second portion 134 of the elongated tubular object 108. Thus, the elongated tubular object 108 may be secured to the second segment of tubing 132 by resistance fit. The resistance fit also creates a watertight seal to prevent any liquid from leaking out from in between the second segment of tubing 132 and the second portion 134 of the elongated tubular object 108. The operative connection of the second segment of tubing 132 to the elongated tubular object 108 can be reversed in that the interior diameter D11 of the second portion 134 of the elongated tubular object 108 can be substantially similar to the outer diameter D12 of the second segment of tubing 132 so as to create a resistance fit. In the event a resistance fit seal or a watertight seal is not created at the operative connection between the second portion 134 of the elongated tubular object 108 and the second segment of tubing 132, a sealant can be used to create a watertight seal or to secure the second portion 134 of the elongated tubular object 108 to the second segment of tubing 132.

Like the first segment of tubing 126, the second segment of tubing 132 is preferably substantially rigid tubing being comprised of a plastic, PVC, metal, or similar materials to provide at least a modicum of structural rigidity to the device 100 to facilitate use of the device 100. In other words, if the device 100 was solely or primarily comprised unreinforced, flexible material, it would likely be more difficult to use for its intended purpose. Thus, in embodiments in which the second portion 134 is flexible or not so rigid, the second segment of tubing 132 can provide structural reinforcement.

As shown in FIGS. 1A-2 appended hereto, but without intention of being so limited, the urine directional device 100 may further comprise a screen 138. The screen 138 may be operatively connected to the free end 133 of the second segment of tubing 132 opposite the elongated tubular object 108 at the distal end 106 of the device 100. In embodiments without the second segment of tubing 132, the screen 138 may be attached to the second end 136 of the elongated tubular object 108 at the second portion 134. The screen 138, if present, preferably is removable from the second segment of tubing 134 or the second end 136 of the generally elongated tubular object 108. This removable screen 138 may comprise FDA approved material(s).

The screen 138 may be incorporated into the device 100 to collect or catch solid objects or discharges, such as kidney or bladder stones, that can come out in the urine so that such objects may be examined and analyzed by medical professionals. As such, the screen can have a plurality of openings that are large enough to allow the urine to pass through while catching typical sized kidney or bladder stones.

The screen 138 can be operatively connected to the second segment of tubing 134 or the second end 136 of the generally elongated tubular object 108 by any fastener 140 that allows for quick and easy fastening and removal, such as clips, hooks, magnets, threading, resistance fit, hook-and-loop fasteners, and the like. As shown in FIG. 1A appended hereto, two clips 139a, 139b can be used on opposite sides to hold or fasten the screen 138 in place. The clips 139a, 139b may hold the screen 138 in place via a latch/closure mechanism, a detent-type mechanism, or a mechanism that uses spring-loaded force to bias the clips to a closed position in which the screen 138 is held on the second end of the generally elongated tubular object. It is contemplated that other types of clips, or other closure devices, may be employed consistent with the size and purpose of the invention described herein.

In some embodiments, to facilitate moving and directing the device 100, the urine directional device may have a handle 150. The handle 150 can be a rod, a knob, a ring, such as a D-ring or O-ring, and the like. The handle 150 can be operatively connected to the elongated tubular object 108. Preferably, the handle 150 is operatively connected near the midsection of the tubular object 108 or towards the distal end 106. As such, the handle 150 can be operatively connected to the second segment of tubing 132, the second portion 134 of the elongated tubular object 108, or any other position along the elongated tubular object 108 that will facilitate the use and control of the device 100.

The present invention is used to facilitate directional urination. In other words, the present invention is used for controlling directional flow of urine during urination. To use the urine directional device 100 described herein, one may simply place the cap 120 over genitalia, such as the penis, aim the distal end 106 of the device 100 into the toilet by bending the elongated tubular object 108 in the proper direction, and then the subject can urinate. After urination, the screen 138, if present, may be detached and the device 100, including the screen 138, can be thoroughly cleaned with a brush 142 and cleanser, such as disinfectant/bacterial soap, bleach-containing product, alcohol-containing product, and the like.

The device 100 can be deployed by the individual urinating (by himself), or by a friend, family member, nurse, or any other caregiver that assists the individual. An additional benefit of the device 100 described herein is that it takes away the embarrassment for both the individual and caregiver having to handle and pull out the penis. Rather, the caregiver would only have to place the product described herein over the genitalia, such as the man's penis, in advance of urination.

The device 100 can be slipped over the penis easily by the individual or caregiver, with minimal or no discomfort because of the cap 120 that contact's the man's body in the area from which the penis extends. Then, the individual or caregiver can aim the distal end 106 of the device 100 towards the toilet to direct the urine into the toilet bowl. The device 100 can then be placed in the nearest sink, tub, shower, or the like to be washed and ready for the next use.

Figure 4:
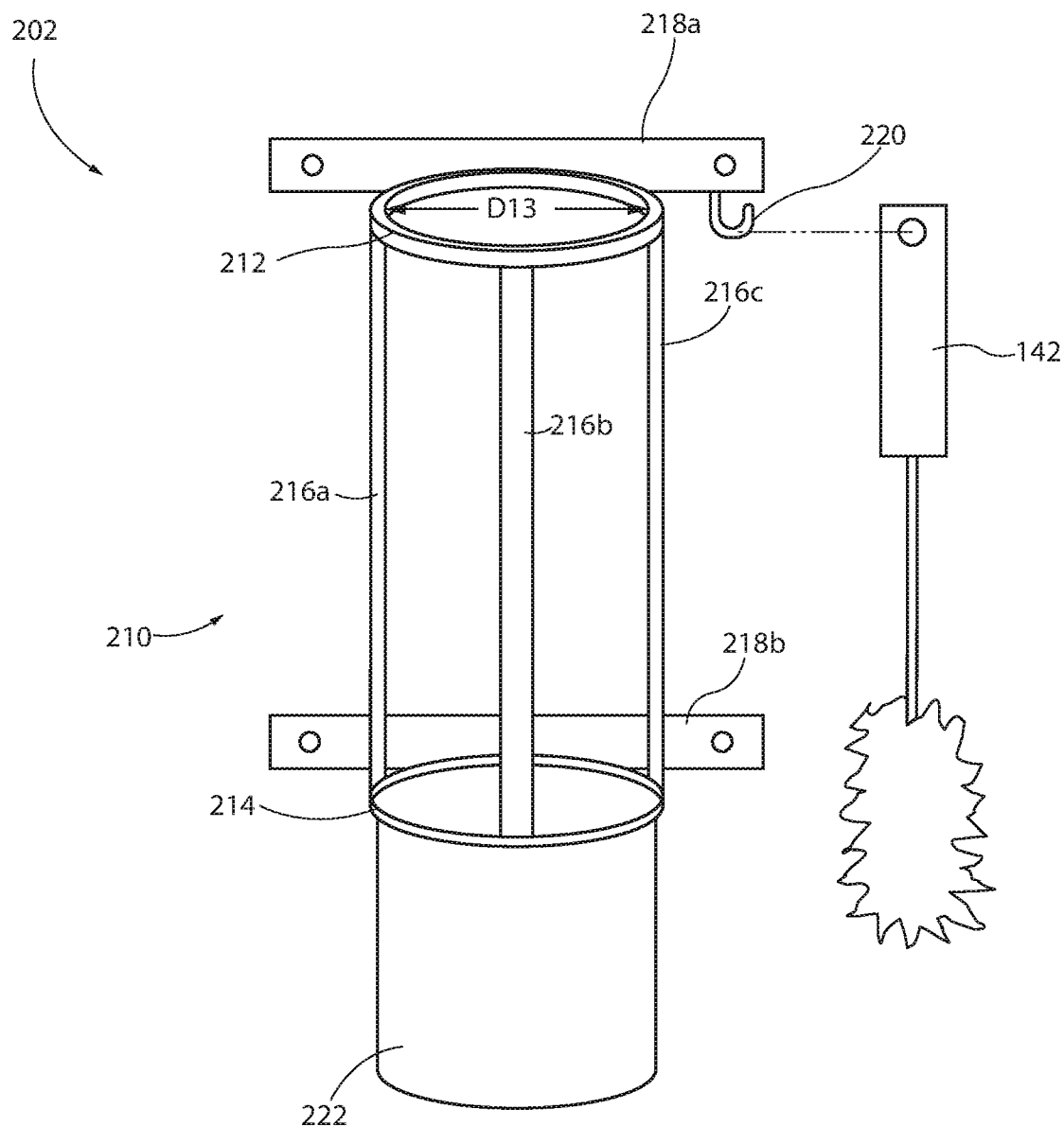
FIG. 4 is a perspective view of a holder.

As shown in FIGS. 3 and 4, the urine directional device 100 can be part of a urine directional device system 200 further including a holder 202, and optionally a cleaner 204. In some embodiments of the system 200 described herein, comprises the urine directional device 100 and a holder 202. The holder 202 provides a convenient means for holding and storing the urine directional device 100. The holder 202 can be any type of hook, hanger, clip, receptacle, container, tie, loop, and the like. In some embodiments, the urine directional device 100 may have a connector to connect the urine directional device 100 to the holder 202 for storage.

In the preferred embodiment, the holder 200 may be generally circular in cross-sectional shape (as is the urine directional device 100) so as to be capable of receiving the urine directional device 100 and hold it for storage and next use. In some embodiments, the holder 200 may be generally a cylindrical receptacle. As such, in some embodiments, the holder 202 comprises a cylindrical frame 210 having a top ring 212, a bottom ring 214, and at least one wall 216 connecting the top ring 212 to the bottom ring 214. If one wall 216 is used, the single wall may form a full cylinder to fully surround the urine directional device 100 when placed inside the holder 202. Alternatively, when more than one wall 216a-c is used, the walls may be intermittently spaced apart along the periphery of the top and bottom rings 212, 214 as shown in FIG. 3. For example, if three walls are used, each wall may be intermittently and evenly spaced apart by approximately 120 degrees. In another example, if four walls are used, each wall may be intermittently and evenly spaced apart by approximately 90 degrees. The spacing between walls 216 do not have to be evenly spaced apart so long as the urine directional device 100 cannot fall through in between adjacent walls 216a-c. The top ring 212 and bottom ring 214 can have an inner diameter D13 that is greater than the exterior diameter D14 of the urine directional device 100. This allows the urine directional device 100 to be placed inside the holder 202.

The holder 202 may be approximately 5 inches to approximately 20 inches long. In some embodiments, the holder 202 may be approximately 7 inches to approximately 18 inches long. In some embodiments, the holder may be approximately 9 inches to approximately 16 inches long. The diameter of the top ring 212 is wide enough to receive the urine directional device 100. For example, the top ring 212 can have a diameter D13 that is at least approximately 0.25 inch greater than the exterior diameter D14 of the elongated tubular object 108. In some embodiments, the diameter D13 can be at least approximately 0.375 inch greater than the exterior diameter D14 of the elongated tubular object 108. In some embodiments, the top ring 212 can have a diameter D13 of at least approximately 0.5 inch greater than the exterior diameter D14 of the elongated tubular object 108. In some embodiments, the top ring 212 can have a diameter D13 of at least approximately 1 inch greater than the exterior diameter D14 of the elongated tubular object 108. In one example, the diameter D13 of the top ring is approximately 2.375 inches.

In some embodiments, the holder 202 may be a partial cylinder so that the urine directional device 100 is simply clipped into the holder 202. The holder 202 can be just the top ring 212, or the top ring 212 and the bottom ring 214.

Preferably, the holder 202 may be affixed to a wall or some other support structure near a toilet via nails, screws, adhesives, magnets, clips, hangers, hooks, hook-and-loop fasteners, or the like. In the preferred embodiment, the holder 202 comprises a mount 218 operatively connected to the top ring 212, bottom ring 214, one or more of the walls 216, or any combination thereof. Preferably, the holder comprises two mounts 218a, 218b, one operatively connected to the top ring 212, and the second mount operatively connected to the bottom ring 214. The mounts 218a, 218b may be in the form of a bracket that can be fastened to the support structure, for example, using standard fasteners that securely fasten the holder 200 to the support structure.

In some embodiments, the holder 202 may also comprise a secondary holder 220 attached to one of the mounts 218a, 218b, the top or bottom rings 212, 214, or the walls 216. Preferably, the secondary holder 220 is attached to the top mount 218a. The secondary holder 220 allows for a cleaning device 142, such as a brush, towel, sponge, or similar cleaning device to be stored adjacent to the urine directional device 100. As such, the secondary holder 220 can be can be any type of hook, hanger, clip, receptacle, container, tie, loop, vertical slot, and the like, onto or into which the cleaning device can be held, hung, supported, slid into, or otherwise, mounted thereon or therein for storage.

In some embodiments, the holder 202 may further comprise an open-top container 222 that can be a removable or disposable bottom element generally circular in cross-sectional shape with a closed bottom. The open-top container 222 can be operatively connected to the bottom of the holder 200, for example, attachable to the bottom ring 214 so as to catch any dripping liquids from the urine directional device 100 to prevent any dripping onto the floor by the urine directional device when it is at rest in the holder 200.

In a removable embodiment, the open-top container 222 may snap, thread, clip, squeeze (resistance fit), or otherwise may securely, but removably, fasten onto a bottom portion of the holder 200, such as the bottom ring 214. If the open-top container collects liquids dripping from the urine directional device 100, it can be easily removed to be cleaned or exchanged. In a some embodiments, the open-top container 222 may be attached to the holder 200 in a manner similar to a disposable cup in a vertical cup dispenser often found adjacent to a water cooler in an office, such that the open-top container 222 may be disposed of after each use.

In some embodiments, to reduce the frequency of cleaning the device 100, the device may comprise an inner liner 224. The inner liner 224 may be an aqueous impermeable membrane that is disposable, for lining the interior surface of the device 100. By way of example only, the liner 224 may be plastic, rubber, or any other FDA approved material(s), or the like. Preferably, the liner 224 is elastic and can be stretched to cover the entire interior surface of the device 100. The elasticity will allow the liner 224 to be stretched over the openings at the proximal and distal ends 104, 106. In some embodiments, the liner 224 is merely flexible. To remove, the user can release one end of the liner 224 and tie it in a knot to contain any remnants inside. Then, the opposite end can be removed and tied in a knot, thereby containing any remnants left inside. As such, the interior of the device 100 remains relatively clean.

The urine directional device 100 is distinct from a catheter, as the device 100 described herein is not inserted into the penis. Therefore, it is much easier and more comfortable to use than a catheter, which has many drawbacks, including a lack of comfort.

Although the invention was described with respect to use by men, this invention is not so limited. The urine directional device can be used on women and animals if such a need should arise. The dimensions of the device can be changed accordingly. The cap portion 120 can be made sufficiently pliable so as to conform to the anatomy of the user to create a tight seal at the appropriate location to reduce leakage.

As discussed above, components of the urine directional device 100 can be constructed as a single, integrally formed component, or as separate components removably attachable to the adjacent components. Thus, in some embodiments, the urine directional device 100 can be disassembled.

The foregoing description of presently preferred embodiments of the invention has been presented for the purposes of illustration and description only. It is not intended to be exhaustive or to limit the invention to the precise form(s) disclosed. Many modifications and variations are possible in light of the above teachings while remaining consistent with the spirit of the invention. It is intended that the scope of the invention not be limited by this detailed description.

The invention claimed is:

1. An urine directional device, comprising:
   a) a cap portion; and
   b) an elongated tubular object having a first end region having a first diameter, a second end region having a second diameter, the second end region opposite the first end region, and a body therebetween, the body having a third diameter, the first end region of the elongated tubular object operatively connected to the cap portion, wherein the third diameter is greater than the first and second diameters, the elongated tubular object defining a first opening, c) wherein the cap portion and the elongated tubular object define a tube having a proximal end, a distal end opposite the proximal end, an interior surface extending from the proximal end to the distal end, and an exterior surface extending from the proximal end to the distal end, the interior surface defining a channel, wherein the cap portion comprises a hollow post and a flanged base towards the proximal end, wherein the first end region of tubing is operatively connected to the cap portion via the hollow post, wherein the cap portion defines a second opening that is continuous with a third opening defined by the hollow post, which is continuous with the first opening defined by the elongated tubular member.

2. The urine directional device of claim 1, wherein the first end region and the second end region of the elongated tubular object are rigid, and wherein the body is flexible.

3. The urine directional device of claim 1, further comprising a screen operatively connected to the second end region of the elongated tubular object opposite the first end region and the cap portion.

4. The urine directional device of claim 1, further comprising a lining covering the interior surface.

5. The urine directional device of claim 1, further comprising a handle operatively connected to the elongated tubular object.

6. The urine directional device of claim 1, wherein the elongated tubular object is accordion tubing.

7. The urine directional device of claim 1,
a) wherein the elongated tubular object is flexible; and
b) wherein the first end region and the second end region are rigid.

8. The urine directional device of claim 7, wherein the flanged base has a diameter greater than an exterior diameter of the hollow post, and wherein the first end region is operatively connected to the cap via the hollow post.

9. The urine directional device of claim 8, further comprising a handle operatively connected to the elongated tubular object.

10. The urine directional device of claim 9, further comprising a screen operatively connected to the free end of the second segment of tubing.

11. The urine directional device of claim 10, further comprising a liner covering the interior surface.

12. A method of controlling directional flow of urine, comprising:
a) placing a urine directional device over a genitalia, wherein the urine directional device comprises an elongated tubular object having a first end having a first diameter, a second end opposite the first end, the second end having a second diameter, and a body therebetween, the body having a third diameter, wherein the third diameter is greater than the first and second diameters; a cap portion operatively connected to a first portion of the elongated tubular object at the first end; wherein the cap portion and the elongated tubular object define a tube having a proximal end, a distal end opposite the proximal end, an interior surface extending from the proximal end to the distal end, and an exterior surface extending from the proximal end to the distal end, the interior surface defining a channel;
b) aiming a second portion of the elongated tubular object into a toilet by bending the elongated tubular object in a proper direction with a handle, whereby direction flow of urine is controlled;
c) removing the urine directional device from the genitalia; and
d) storing the urine directional device in a holder, the holder comprising a cylindrical receptacle and an open-top container connected to a bottom of the cylindrical receptacle, wherein the elongated tubular object fits within the cylindrical receptacle.

13. The method of claim 12, further comprising contracting the urine directional device prior to storing the urine directional device in the holder.

14. The method of claim 13, further comprising removing the open-top container from the bottom of the cylindrical receptacle to discard waste collected in the open-top container from the urine directional device.

15. The method of claim 12, further comprising removing a screen from the free end of the second segment of tubing to collect solid discharge trapped in the screen.

16. A system for controlling directional flow of urine, comprising:
a) a urine directional device, comprising:
(i) a cap portion, and
(ii) an elongated tubular object having a first end region, a second end region opposite the first end region, and a body therebetween, the first end region of the elongated tubular object operatively connected to the cap portion, wherein the body is cylindrical and flexible, and wherein a handle is connected to the body;
(iii) wherein the cap portion and the elongated tubular object define a tube having a proximal end, a distal end opposite the proximal end, an interior surface extending from the proximal end to the distal end, and an exterior surface extending from the proximal end to the distal end, the interior surface defining a channel; and
b) a holder configured to receive the urine directional device.

17. The system of claim 16, further comprising a cleaning device mountable on the holder.

18. The system of claim 16, further comprising a removable open-top container operatively connectable to the holder.

* * * * *